United States Patent [19]
Techiera et al.

[11] Patent Number: 6,096,043
[45] Date of Patent: Aug. 1, 2000

[54] EPICONDYLAR AXIS ALIGNMENT-FEMORAL POSITIONING DRILL GUIDE

[75] Inventors: Richard C. Techiera, Avon, Mass.; Arlen D. Hanssen, Rochester, Minn.; Scott Presbrey, Slatersville, R.I.

[73] Assignee: DePuy Orthopaedics, Inc., Warsaw, Ind.

[21] Appl. No.: 09/216,436

[22] Filed: Dec. 18, 1998

[51] Int. Cl.$^7$ ............................................... A61B 17/58
[52] U.S. Cl. ............................................. 606/88; 606/87
[58] Field of Search ........................... 606/87.88; 623/20

[56] References Cited

U.S. PATENT DOCUMENTS

| | | |
|---|---|---|
| D. 367,706 | 3/1996 | Stalcup et al. .......................... D24/140 |
| D. 369,863 | 5/1996 | Hayes ..................................... D24/155 |
| 4,524,766 | 6/1985 | Petersen ................................. 128/92 H |
| 4,722,330 | 2/1988 | Russell et al. ............................. 606/88 |
| 4,759,350 | 7/1988 | Dunn et al. ......................... 128/92 VW |
| 5,395,377 | 3/1995 | Petersen et al. ........................... 606/88 |
| 5,443,518 | 8/1995 | Insall ........................................ 623/20 |
| 5,458,645 | 10/1995 | Bertin ....................................... 623/20 |
| 5,474,559 | 12/1995 | Bertin et al. ............................... 606/88 |
| 5,540,696 | 7/1996 | Booth, Jr. et al. ......................... 606/88 |
| 5,688,280 | 11/1997 | Booth, Jr. et al. ......................... 606/88 |

OTHER PUBLICATIONS

Thomas S. Thornhill, et al. "Revision Surgery for Failed Total–Knee Replacement"—Johnson & Johnson Orthopaedics SP2–008 (1997).
Richard D. Scott, et al. "Primary Cruciate–Retaining Procedure"—Johnson & Johnson Orthopaedics, pp. 1–55.
Richard A. Berger, M.D., et al. "Determining the Rotational Alignment of the Femoral Components in Total Knee Arthroplasty Using the Epicondylar Axis" Determining Femoral Roitation in TKA, Clinical Orthopaedics and Related Research, pp. 40–47, No. 286, Jan., 1993.

*Primary Examiner*—Michael Buiz
*Assistant Examiner*—Julian W. Woo
*Attorney, Agent, or Firm*—Nutter, McClennen & Fish, LLP

[57] ABSTRACT

A tool lays out resection or alignment features to prepare a bone end for prosthetic joint replacement. The tool attaches to the end of the femur, and positions an initial cut, for example a pair of aligned drill holes for the positioning pins of a prosthesis or the cutting blocks used in preparing the distal femur. The tool includes adjustable assemblies coupled to a main body for setting its position, and these are arranged with graduations for sizing the femur. The adjustable assemblies include an epicondylar engaging assembly such as a pair of clamp arms which slide in the body to align the body along the epicondylar axis. It further includes one or more other assemblies which determine a line, offset depth or other coordinate or component of orientation to set the drill guide for optimally locating the initial cut in the femur. Preferably, the other assemblies include an A/P sizing jig in the tool which determines an offset, and the drill guide is coupled so that it positions drill holes on the bone end in coordination with sizing jig. The clamp assembly may further indicate medial/lateral offset information for shifting the center to improve tracking and alignment. This allows the surgeon to confirm or adjust both the size and the position of the prosthesis with respect to several landmarks using a single tool. The drill holes may set a position for a standard cutting block to fit the femoral end component of a prosthetic knee.

12 Claims, 6 Drawing Sheets

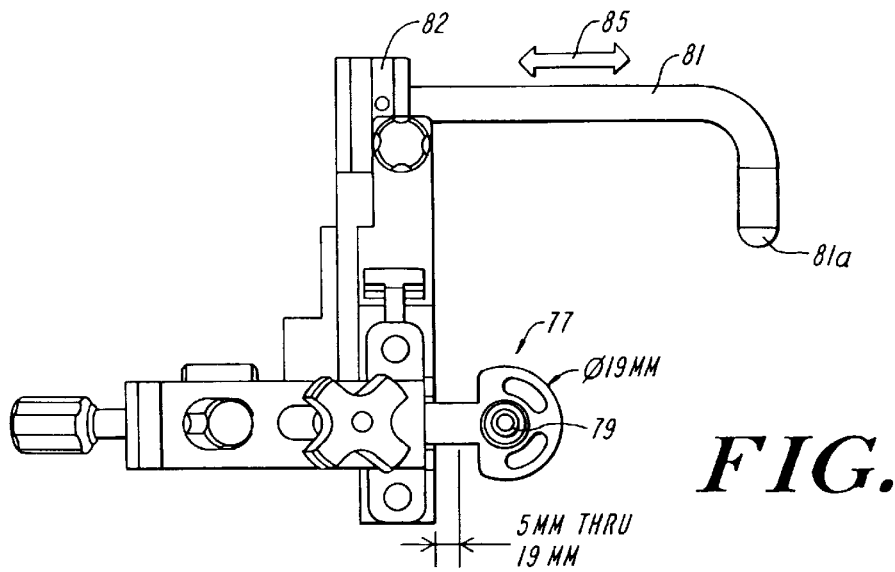
FIG. 2A
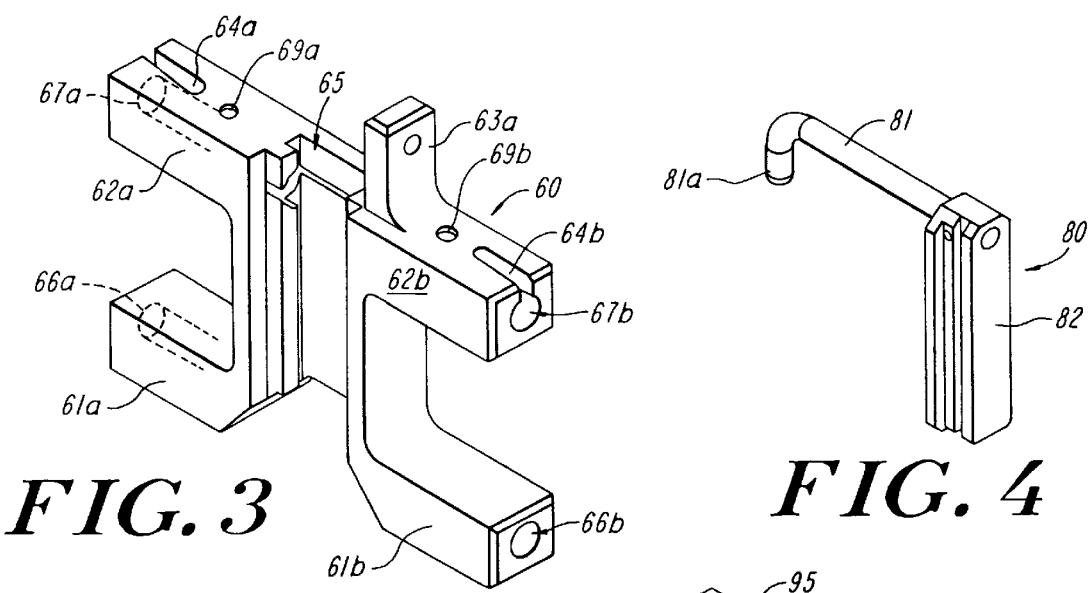
FIG. 3
FIG. 4
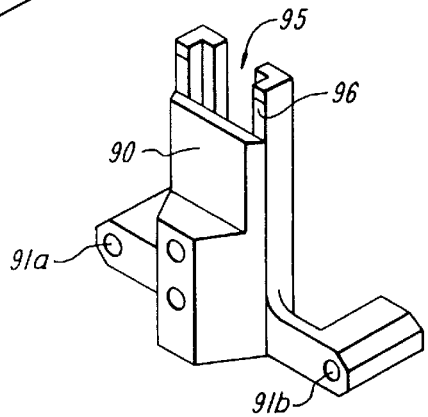
FIG. 5

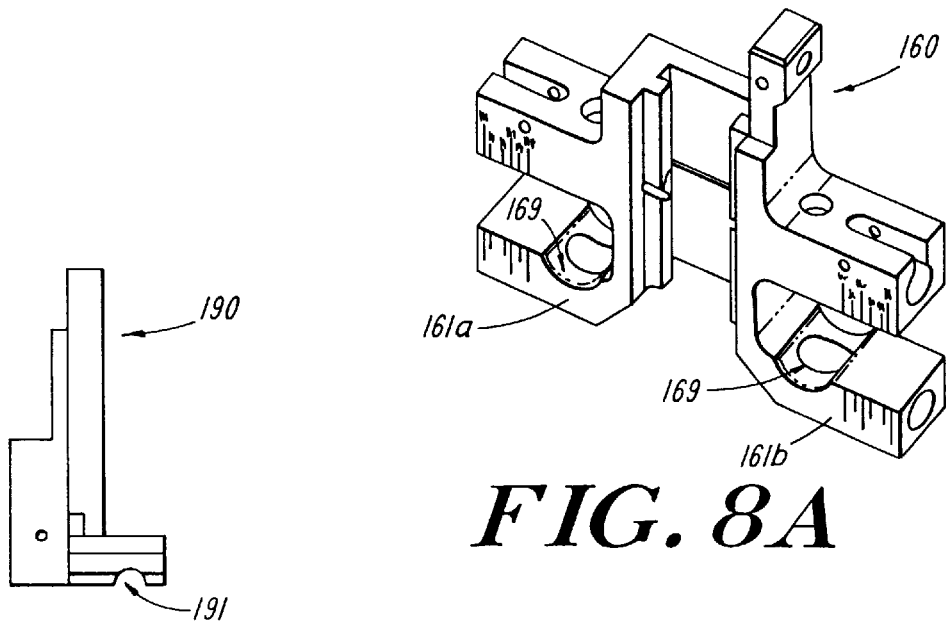
FIG. 8A
FIG. 8B
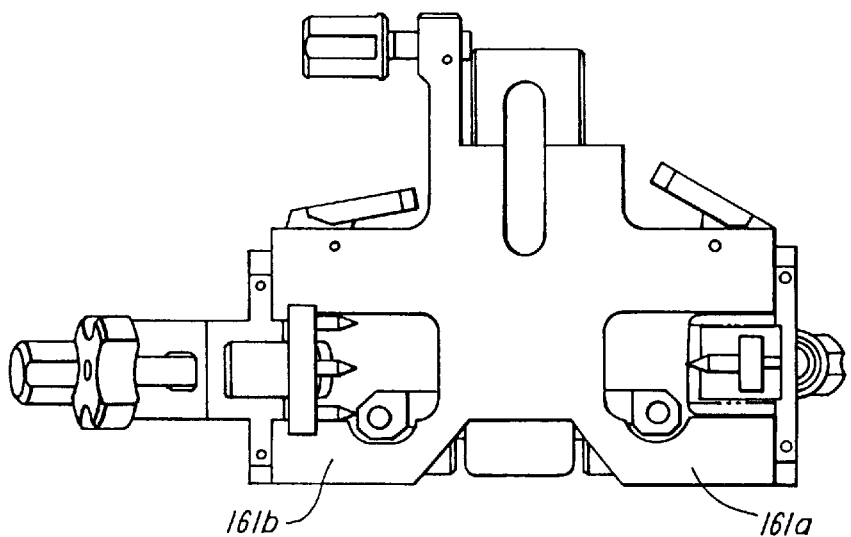
FIG. 8C

EPICONDYLAR AXIS ALIGNMENT-FEMORAL POSITIONING DRILL GUIDE

CROSS-REFERENCE TO RELATED APPLICATIONS

Not applicable.

STATEMENTS REGARDING FEDERALLY SPONSORED RESEARCH

Not applicable.

FIELD OF INVENTION

The present invention relates to tools and jigs for laying out machine cuts to prepare a bone for receiving a correctly sized and aligned prosthetic component, such as a component of a prosthetic knee joint assembly.

BACKGROUND OF THE INVENTION

The surgical preparation of bone endings for receiving prosthetic knee joints for a total knee replacement is generally a complex procedure, particularly when ligaments remain attached, or when osteoarthritic changes to the joint have distorted the normal, more symmetric articulation geometry of the joint or bone. In general, it is necessary to perform soft tissue balancing and numerous specially aligned cuts at the bone ends in order to install the prosthetic components with correct spacing, alignment and tensioning to prevent improper kinematics from arising as the joint rotates in use, and to avoid the occurrence of accelerated wear patterns or possible joint dislocation.

A number of bone cuts are made to effect the placement and orientation of the femoral component of the prosthesis on the bone with the appropriate joint gaps in extension and flexion. The size and shape of these two bone gaps affect final bone orientation as well as joint tensioning and clearances when the prosthesis is installed. With respect to their effect on final orientation, the flexion gap is related to internal/external orientation of the femur, while the extension gap is related to the varus/valgus orientation of the femur.

Generally, these cuts are formed so that in extension the joint gap is perpendicular to the mechanical axis of the femur, while in flexion the joint gap is such as to place the femoral component in either neutral or external rotation and achieve patellar tracking with the femoral component. Furthermore to fit the femoral component the gaps created by the bone resections in both flexion and extension should be rectangular. In flexion, the relevant natural articulation surface corresponds to the tangent plane of the posterior epicondyles, and in extension, to that of the distal epicondylar surface. However, by performing A/P cuts by reference to the posterior surfaces, there is some risk of notching the anterior cortex. Thus, many surgeons set the A/P cut positions with reference to the anterior cortex. In one surgical protocol, the fitting is done after first resecting the distal femur, drilling positioning holes for the femoral joint component positioning pins, and then placing one or more cutting blocks or other tool alignment assemblies in the positioning holes to prepare various surface cuts.

Typically this requires a number of measurement steps and cutting or fitting steps, often with additional small adjustment cuts to achieve the final bone preparation. However it is difficult to devise a jig which dependably sets the femoral alignment because landmarks may be inconsistent or obscure. In general, the surgeon must exercise judgment as the various cuts are made. Also the steps in reaching a determination will vary depending upon the initial landmarks used for setting preliminary resections, both as a matter of the surgeon's preferred procedure and as constrained by any patient-specific features or disease.

Recently, some interest has arisen in using the epicondylar axis as a guide line, either by marking its position as a reference for slight adjustment to be made during fitting, or as a primary landmark when disease or a previous arthroplasty have altered or obliterated other landmarks. When used to set internal/external rotation this provides improved balance of the collateral ligament tension between flexion and full extension. However, it can be awkward to determine the epicondylar axis, and while the clinical epicondylar prominence may be considered in advance of surgery, the sequence of steps required to harmonize preparatory cuts with the epicondylar surfaces or opposed articulation elements of the prosthesis remains complex.

Accordingly, it would be desirable to provide a tool to simplify procedures during surgery for sizing and performing preparatory bone cuts, or for setting alignment marks to prepare the bone to receive a prosthetic joint component.

It would further be desirable to provide such a tool which aligns with the epicondyles of an exposed femur and determines one or preferably several features or measurements, such as prosthesis size, centerline and A/P offset, to enable a fitting procedure with standard cutting blocks referenced to the epicondylar axis.

SUMMARY OF THE INVENTION

A tool in accordance with the present invention lays out resection or alignment features for prosthetic joint replacement. The tool attaches to the end of the femur, and includes adjustable assemblies coupled to a main body for setting the alignment and determining size of a prosthesis, for example by drilling positioning holes or otherwise setting one or more preparatory cuts. The adjustable assemblies include an epicondyle clamp assembly and a cortex hook assembly, each of which slides in the body to determine a line, depth or other component of orientation of the assembly, which locates a drill guide to place positioning pin holes accordingly in the femur. Once aligned by the clamp, a sizing jig in the tool determines an offset, which may be confirmed or adjusted by reference to the cortex hook setting. A drill positioning block is coupled to the various sizing assemblies so that it positions drill holes on the bone end in coordination with the size and preferably one or more offset indicators which confirm or adjust the size or position with respect to different landmarks. The drill holes may set a position for standard cutting blocks to complete fitting of a femoral end component.

BRIEF DESCRIPTION OF THE DRAWINGS

The foregoing features of this invention, as well as the invention itself, may be more fully understood from the following description of the illustrative embodiments, taken together with the drawings in which:

FIG. 2A is a side plan view from the medial side of that embodiment;

FIG. 3 is a perspective view of a central body component of the prototype embodiment shown in FIG. 2;

FIG. 4 is a perspective view of an A/P setting component thereof;

FIG. 5 is a perspective view of a drill guide component thereof; and

FIGS. 8A–8C illustrate another embodiment of the device with enhanced A/P sizing range.

DETAILED DESCRIPTION OF THE INVENTION

The present invention is a tool which simplifies the procedure of preparing the distal femoral end for a prosthetic implant by allowing the surgeon to conveniently size the femur and position components in relation to the epicondylar axis using a single instrument. The mechanical arrangement of various components of the tool in a prototype embodiment 50 will be appreciated from discussion of the figures below, illustrating its structure and operation.

Figure 1:
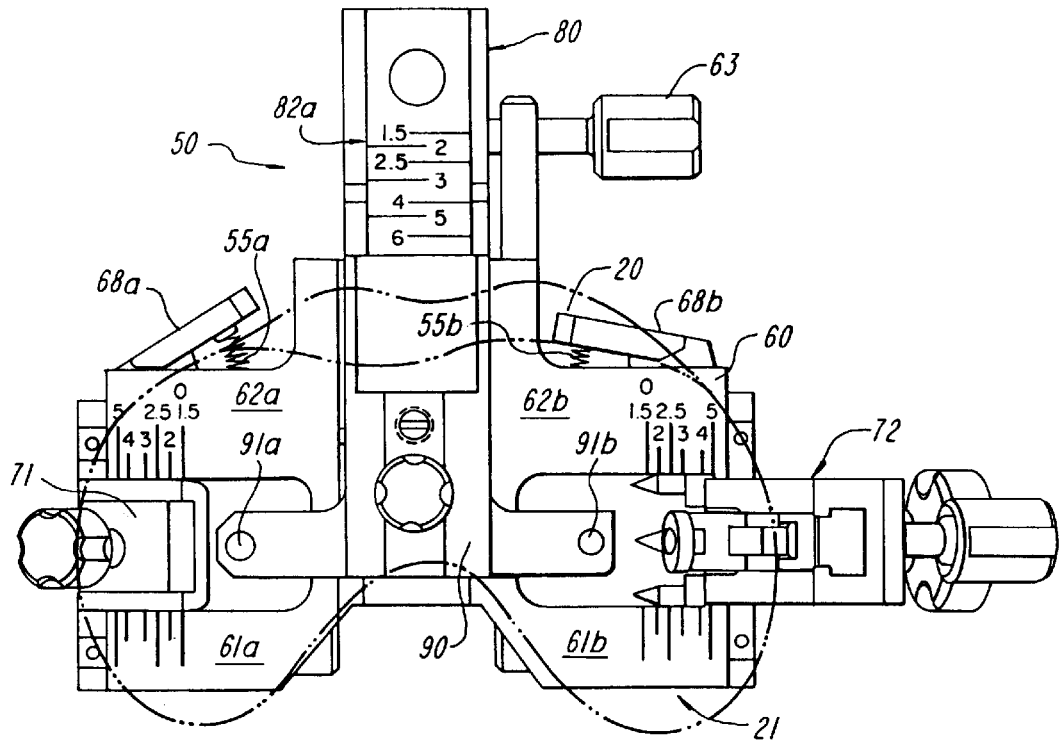
FIG. 1 illustrates one embodiment of the tool according to the present invention on a distal femur end.

FIG. 1 shows a front plan view of a prototype embodiment of the tool 50 of the present invention, configured for use during surgery so that it lies across the distal resected end of the femur 20. For clarity of exposition in the discussion which follows, an end view of the femur is drawn over the tool, although it will be appreciated that in use, the femur would lie behind the tool (in the illustrated front view), and be largely obscured by the mechanisms thereof, with only its outline and certain central portions of the bone face visible.

By way of overview, the tool is preferably used once the surgeon has made the distal femoral cut, and includes a central body 60 which is positioned across the distal bone end by a clamp assembly 70 having two clamp arms, 71, 72 that slide in the body 60, or are otherwise mounted to secure the orientation of the body 60 with respect to the clamp 70 as it grips the epicondyles at their central regions where the collateral ligaments attach. Another positioning assembly 80 slides in the body 60 in a cross direction, vertically (corresponding to the A/P direction across the distal resection with the femur in flexion), and this assembly carries an A/P drill positioning plate 90 having drill positioning holes 91a, 91b for locating the positioning pin holes of a prosthesis and/or the pins of a preparatory cutting block. Together the clamp 70 and A/P positioning assembly 80 orient and position the drill plate 90 so that the pin holes are drilled on the end of the femur with an A/P offset, discussed further below, and are oriented along the epicondylar axis. As further shown in the figure, sizing graduations aid in determining an appropriate size femoral component, or in adjusting the size or location with respect to different landmarks contacted by the epicondyle clamp assembly or the A/P contact stylus of the assembly 80, or with respect to the outline of the resected distal bone surface 21.

As shown in this view, the central body 60 has left and right pairs of substantially horizontal arms 61a, 62a and 61b, 62b to which the clamp sub-assemblies 71, 72, respectively, are carried.

Figure 2:
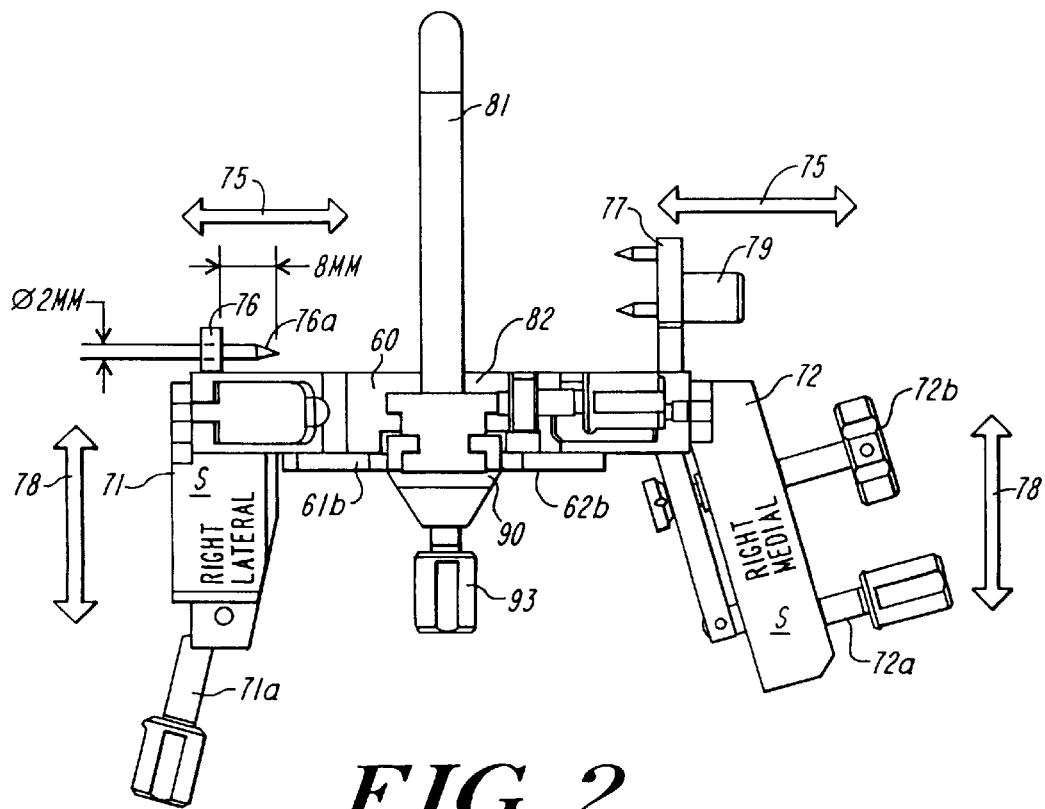
FIG. 2 is a top plan view of the tool shown in FIG. 1 illustrating relevant features.

FIG. 2 shows a top plan view of the tool 50 of the prototype embodiment of FIG. 1, better illustrating features of its construction and the configuration of various submodules of the prototype assembly.

Clamp arm assemblies 71, 72 having different structure from each other are shown at the left and right sides, respectively, of the central body 60. It should be noted however, that preferably the clamp arms 71, 72 mount interchangeably on either the left or the right side of the assembly. In FIGS. 1 and 2, clamp arm 71 is configured to engage the lateral epicondyle, and it is placed on the left side of the assembly 60, while clamp arm 72 is configured to engage the medial epicondyle, and is placed on the right side of body 60. As so assembled, the tool is set up for use on the right femur; i.e., clamp 71 grips the lateral epicondyle of the right femur, and clamp 72 engages the medial epicondyle of the right femur. When the sides of the arms are interchanged in the central body 60, the arms would then be configured for engaging the epicondyles of the left femur. Reversal of the two arms involves turning them upside down and placing them on the opposite (left or right) side of the body 60.

The tool thus has a handedness symmetry. To indicate the functional structure of each arm 71, 72, the upper and lower surfaces S of each arm assembly therefore bear a permanently inscribed legend indicating whether it is a medial, or lateral engager, and whether it is in the orientation for the right or the left femur. In the set up of FIG. 2, the arms are attached in position for engaging the lateral and medial epicondyles of the right femur, and the appropriate legend "right medial" or "right lateral" is visible to the surgeon.

Continuing with the discussion of FIG. 2, the overall structure of the prototype embodiment 50 is implemented with the vertical post of the A/P positioning assembly 80, which is here configured like a cortex hook, being formed as a double T-beam 82 upon which the central body 60 and the drill positioning plate assembly 90 are each carried by sliding along T-slots into which the post 82 fits. Thus, both the clamp body 60 and drill plate 90 may be adjusted in vertical position with respect to the post 82. Respective locking knobs 63 (FIG. 1) and 93 are provided to lock them in a desired vertical position, discussed below. Thus each of the three major components may be shifted in the vertical direction. As further shown in FIG. 2, a hook member 81 extends out from the face of the vertical post 82 to contact the anterior surface of the femur. Cortex hook 81 is attached in the assembly 80 and is used to set the offset of the other components from the anterior face of the bone. The cortex hook 81 slides in a proximal/distal direction without rotation through its mounting in the post 82, as indicated by the adjustment axis arrow 85 (FIG. 2A), and may be locked, e.g. by a screw or detent (not shown).

Returning briefly to the front view of FIG. 1, it will be seen that a series of scored grooves and graduated size markings indicated generally by 82a are scribed on the post 82, with the graduations corresponding sizes of the femoral component. By setting the drill positioning plate 90 at the appropriate previously determined size, the drill holes 91a, 91b are placed at the proper A/P position for that size component. As best seen in FIG. 1, the drill positioning plate carries the drill positioning holes 91a, 91b in horizontally-extending arms which move between upper and lower positions in the space between the horizontally extending arms 61, 62 of the central body that hold the epicondylar clamping assembly.

The construction and mounting of various components forming the epicondylar clamping assembly will be better understood from FIGS. 3, 6A, B and 7A, B, C discussed below. FIG. 3 shows a perspective view of the central body 60 of FIG. 1. As shown, a protruding body portion 63a accommodates the locking screw 63 of FIG. 1 at a position adjacent to the T-slot 65, so that the screw bears against the vertical post 82 of the A/P positioning assembly 80 to lock the vertical position of the body 60. Further, each of the arms of the central body to which the clamping assemblies 71, 72 are attached, include a set of support/alignment bores or guide holes (67a, 67b in the upper arm 62 and 66a, 66b in the lower arm 61) in which the respective clamping arms are mounted for sliding side to side in the horizontal plane. Thus, the central body 60 and clamping assembly are positioned as a unit on the post 82 against the distal femur resected face 21.

Figure 9A:
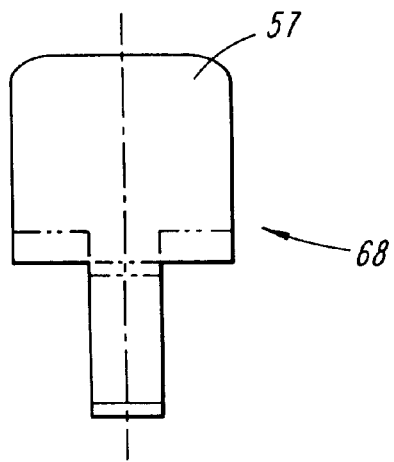
FIGS. 9A, 9B and 9C are front, side and perspective views of ratchet release levels of the embodiment shown in FIGS. 1–4.
Figure 9B:
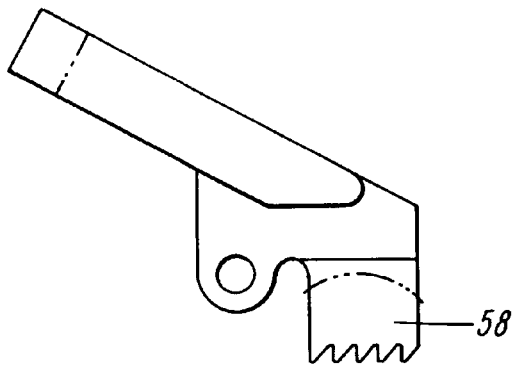
Figure 9C:
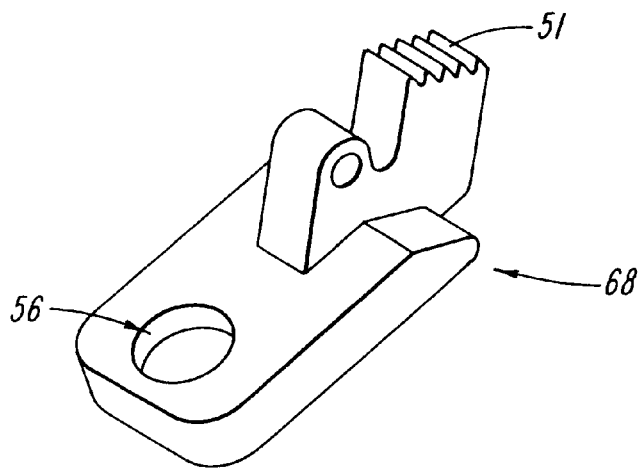

Ratcheting release levers 68a, 68b shown in FIG. 1 lock the position of the clamp arms 71,72 once they grip the epicondyles, thus setting both the inter-arm spacing and the relative position of the central body 60 with respect to each of the two clamping arms. FIGS. 9A, 9B and 9C illustrate the release/locking elements of the prototype construction in greater detail. As shown in FIG. 2, on each side of the top of the central body upper arms 62 are slots 64, which extend into the guide holes 67. Two spring-loaded ratchet release levers 68 each have a central protrusion 58 which fits into the corresponding slot 64. On the top of the lever protrusion 58 are multiple grooved serrations 51 which match the serrations 53 (FIG. 6B) on the clamp arm rails 71, 72, and serve as ratcheting lock mechanisms as those rails are extended. Squeezing a lever 68 disengages the serrated edge of the lever and allows the clamp arm 71 or 72 to slide in its guide bores 66, 67 of the body 60. Releasing the lever locks the clamp arms in the set position.

As further shown in FIG. 3, blind holes 69 adjacent to each slot 64 on the top of the central body upper arms 62, act as seats to hold one end of a locking lever spring 55. A corresponding blind hold 56 (FIG. 9C) is formed on the underside of the lever at the thumb-pad region 57, and this holds the opposite end of the spring 55 to bias the serrations in an engaged position.

In FIG. 2, both the clamping assemblies 71, 72 are illustrated fully-collapsed in their sliding mounts, but it will be understood that each is capable of several centimeters of sliding motion horizontally out from the center to position their respective gripping portions on the epicondylar features of interest. This range of motion is indicated by adjustment arrow 75 in the Figure. As further shown, each clamp arm includes an epicondyle-engaging tip portion 76, 77 which may be moved back and forth in direction indicated by arrows 78 and locked in position by a corresponding locking screw 71a, 72a.

As further seen in FIG. 2, the gripping end 76 of the lateral side epicondylar engager contains a single central protruding pin 76a which extends approximately eight millimeters centrally inward from the arm, while the engaging tip 77 of the medial side epicondylar engagement arm contains a plurality of pins which are preferably arranged as shown in FIG. 2A, substantially concentrically around a drill guide 79 that positions a drill to drill a central hole in the epicondyle for receiving the epicondylar anchor pin. A clamping screw 72b urges the pin assembly of the medial tip 77 centrally inward for gripping the epicondyle once it is correctly positioned over the center of attachment of the medial collateral ligament.

FIG. 2A is a side plan view from the medial side of the assembly 50 of FIG. 2. As shown, the epicondylar engaging assembly 77 of this embodiment has generally a skeletal or frame-like structure forming a template which allows convenient visualization of the region of attachment of the medial collateral ligament as the engaging head 77 is brought into position, so that the epicondylar pin drill guide 79 may be visually centered in position. In general, the clamp arm is set to extend between about five and twenty five millimeters from the face of the central body 60, thus assuring that it is positionable to cover the full range of depth at which the epicondylar axis may to be located. As further seen in FIG. 2A, the cortex hook 81 extends generally perpendicularly to the plane of the body 60, with a stylus tip 81a bending down to contact the anterior femoral surface behind the cortex.

In use, the body 60 is clamped by the assembly 60, 71,72 along the epicondylar axis, and the femur size is next set. This is done by positioning the central body 60 on the resected femoral face and reading off the size indicated by the left and right side graduations on the arms 61,61. This size is then also set on the drill guide by placing the cortex hook stylus in contact with the anterior femoral surface, and then sliding the drill guide plate 90 vertically on the post 82 so that its sizing scribe mark 96 (FIG. 5) lines up with the indicated size on the A/P graduation scale 82a (FIG. 1). The guide plate 90 is locked into place by tightening the thumb screw 93 when the graduation reads the desired implant size. This sets the proper A/P offset of the positioning pin holes for the selected prosthesis size.

Advantageously, the contour of the distal femoral face is clearly visible above and between the arms 61, 62, so that, once the A/P size is set, any misalignment of the standard position on the bone end due to anomalous bone shape or the like is immediately apparent. In case of such misalignment, the assembly may be shifted and a more appropriate size may be read on the graduation scale. The fit of this different size prosthesis may then also be evaluated by re-setting the guide 90 accordingly. When the proper fit is achieved, holes are drilled into the distal resected femur using the drill positioning guide holes 91a, 91b. The device is then removed and surgical technique proceeds using standard A/P cutting blocks pinned in the two drill holes so made.

FIG. 4 illustrates the double T bar 82 which forms part of the A/P positioning assembly, and which allows independent vertical positioning of the drill plate and the epicondylar clamp assembly. As shown, the bar or post 82 includes an edge contour constituting a set of front and rear rails, which fit within the respective T-slot 95 of the drill plate 90 (FIG. 5) and T-slot 65 of the central body 60 (FIG. 3) to independently slideably carry these two assemblies.

Figure 6A:
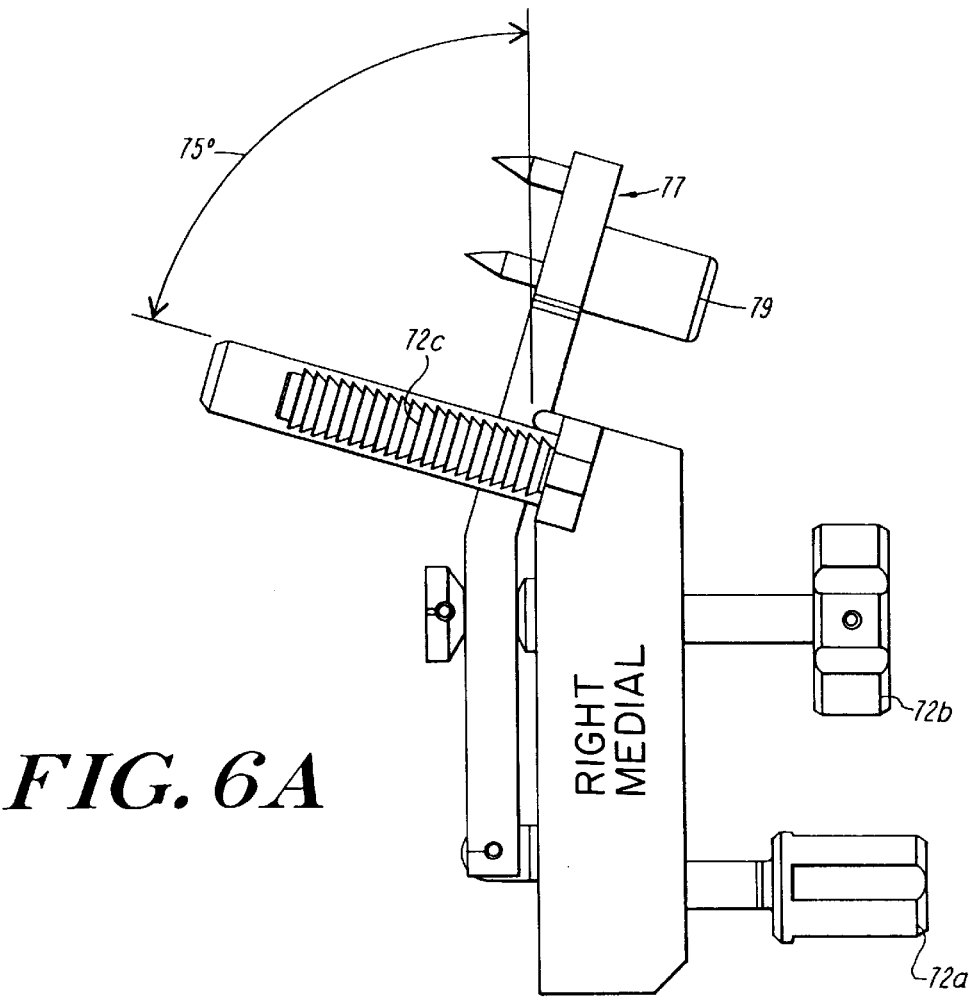
FIGS. 6A and 6B are top and front plan views, respectively, of a first clamp component thereof.
Figure 6B:
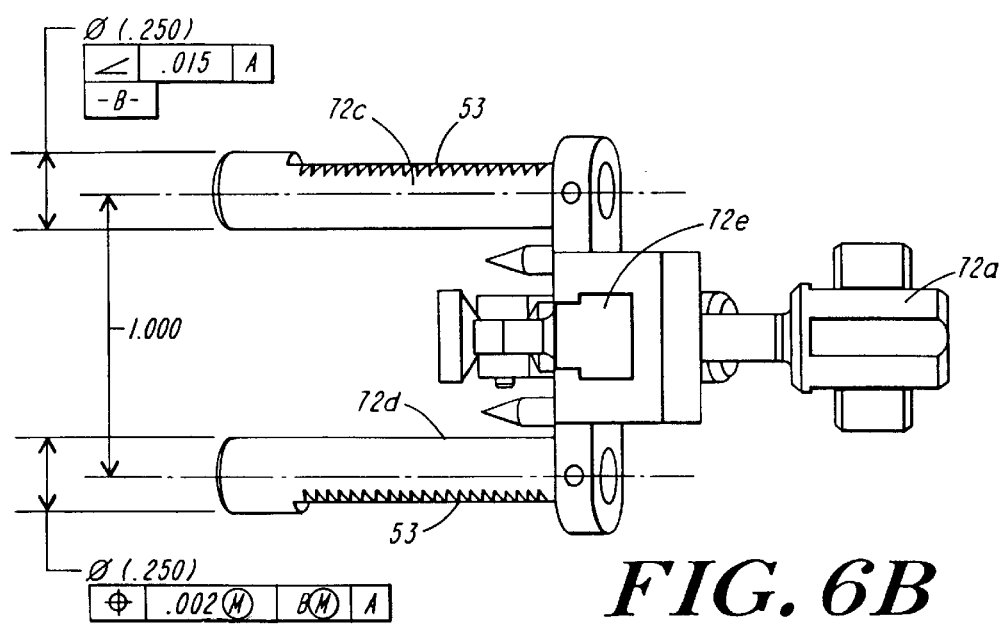

FIGS. 6A and 6B illustrate further details of the clamp arm 72 in top and front plan views, respectively. As shown, the arm includes double support bars 72c, 72d which fit in the guide bores 66b, 67b (FIG. 3) and allow the assembly to slide and lock in the horizontal (medial-lateral) direction. The assembly also includes a slide block 72e which slides in a body to fix the depth extension of the gripping end 77. A thumbscrew 72a locks the position of the slide block 72e, which carries a levered arm. The levered arm in turn is urged inwardly or outwardly by action of the screw 72b to urge the prongs into the medial epicondyle.

Figure 7A:
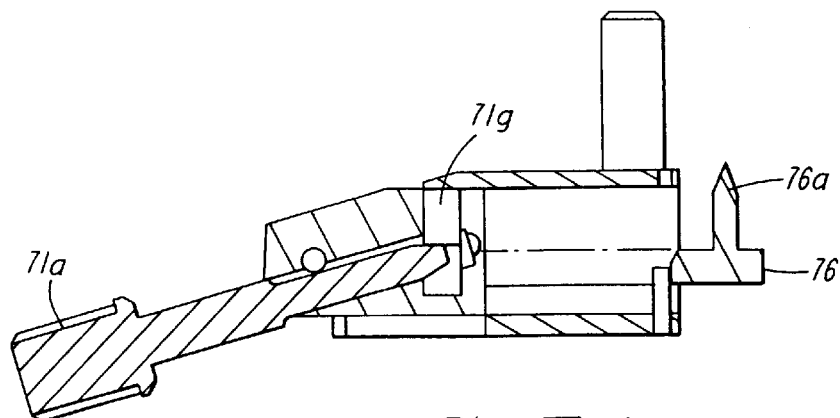
FIGS. 7A, 7B and 7C are a horizontal sectional view, and rear and side plan views, respectively, of a second clamp component thereof.
Figure 7B:
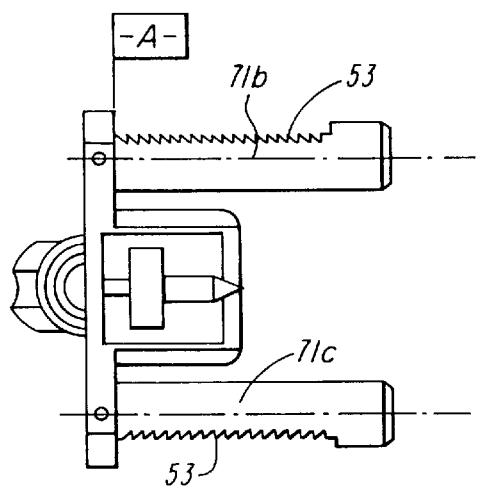
Figure 7C:
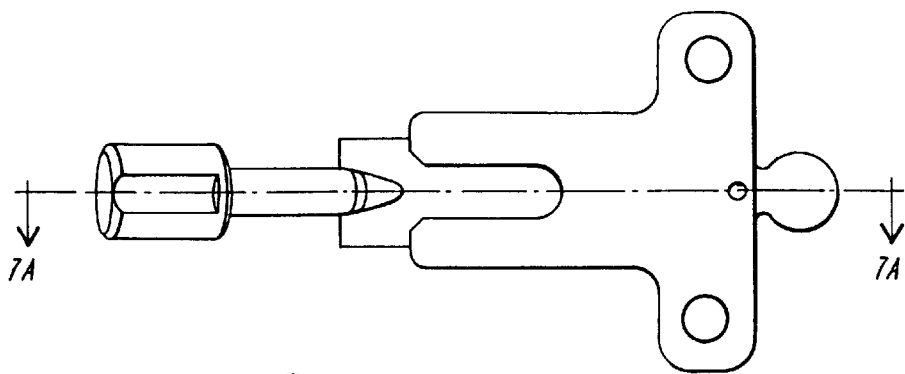

FIGS. 7A, 7B and 7C illustrate the lateral side epicondylar clamping arm 71. Like the medial side assembly, it is slideably carried parallel to the horizontal axis by two arms 71b, 71c that ride in the bores 66a, 67a of the central body. However it has a single, centered prong 76a at its engaging end 76, and this moves back and forth in a cross direction to engage the epicondyle, and is locked by a simple screw mechanism 71a acting on an expanding wedge plate or camming body 71g carried by the arm. By way of example, the gripping ends of the epicondylar clamps preferably independently extend from a minimum extension position about five to eight millimeters past the face of the device, to a maximum extension position about 25 millimeters from the plane of the distal end resection.

The tool as described above has several gauging or positioning components that advantageously in this embodiment position drill holes from which the subsequent cuts are made by simply affixing a standard set of cutting blocks. While the overall structure is a somewhat frame-like or skeletal assembly which accommodates the desired telescoping adjustments without occluding the distal femoral resected surface, the structure may still limit the attainable size readings or position offsets. This limitation is addressed in another embodiment by providing members, such as the drill guide plate 90 and central body 60, which have respective contours or cut-outs whereby one component accommodates the other without interference over an extended range of positional movement. FIGS. 8A–8C illustrate such an embodiment. As shown, a central body 160 similar to the body 60 of FIG. 1 has its lower cross arms 161a, 161b modified by relief cuts 169 which extend across the arms and their clamp bar guide bores. Similarly, the drill guide plate 190, seen in side view in FIG. 8B is notched across the its drill guide bores to remove the solid circumferential wall in the plane where it crosses and would otherwise bump into the arms 161a, 161b. The two components, when mounted on the A/P setting bar thus interfit as shown in FIG. 8C. As seen in that figure, the respective cut-outs or offset edges of the body parts then cross and interfit such that the drill guide holes at their extreme low position pass perpendicularly to the axis of the cross bar bores, and are tangent thereto, so that no solid portion of the bodies contact in that region and each of the bores may accommodate its respective arm 71c, 72d or drill without hindrance. In practice, this offset relief construction of crossed tangent holes for the drill guide and support bores allows the drill guide plate to extend downward an additional 3.5 millimeters in the A/P direction, extending the sizing ability of the tool.

This completes a description of a basic embodiment of the sizing and positioning tool of the present invention and its mode of use in positioning an initial cut or drill hole and sizing the femoral prosthetic component. It will be appreciated that by providing these capabilities in a single instrument, numerous separate adjustments which may otherwise need to reference different landmarks or preparatory cuts, or which require extensive time for setting up and repositioning tools, are replaced, simplifying the overall procedure for preparing the bone to fit a prosthesis. Moreover, in positioning off the epicondylar prominence, a true axis of rotation is identified, simplifying the balancing of soft tissue tension, and permitting a dependable reference for secondary arthroplasty which is readily deployed during the surgery. This permits several practical adjustments of size or position to be carried out with enhanced control or perception of the resulting component fit.

The invention being thus disclosed in a representative prototype embodiment, further variations and modifications will occur to those skilled in the art, and all such variations and modifications are considered to be within the scope of the invention has set forth herein and defined by the claims appended hereto.

What is claimed is:

1. An alignment jig for locating a cutting block or the like to prepare a bone ending for receiving a prosthetic joint component, wherein the bone ending possesses medial and lateral epicondyles defining an epicondylar axis, the jig comprising a body configured to lie adjacent a distal prepared femoral bone surface an epicondylar alignment assembly configured for aligning with the medial and lateral epicondyles and moveably coupled to the body so as to hold the body aligned along the epicondylar axis at said surface an A/P positioning assembly movably extending from the body and being positionable in contact with the bone to set an A/P position of the body, and a tool guide carried by the body for positioning an instrument to make a preparatory cut in the bone whereby the instrument is positioned to make the preparatory cut in alignment relative to the epicondylar axis.

2. An alignment jig according to claim 1, wherein said epicondylar alignment assembly includes clamp arms having engagement prongs for engaging said epicondyles.

3. An alignment jig according to claim 2, wherein one of said clamp arms includes a template for visually centering the engagement prongs on a connective tissue bundle anchored at one of said epicondyles.

4. An alignment jig according to claim 1, wherein one or more elements of said body, said alignment assembly, said A/P positioning assembly and said tool guide, includes size graduations keyed to relative position of said elements for movably adjusting positions of said elements and the body while visually assessing fit of prosthesis size.

5. An alignment jig according to claim 1, wherein two or more elements of said body, said alignment assembly, said A/P positioning assembly and said tool guide, includes size graduations keyed to relative position of said elements for movably adjusting positions of said elements while visually assessing fit of prosthesis size.

6. An alignment jig according to claim 1, wherein three or more elements from among said body, said alignment assembly, said A/P positioning assembly and said tool guide, include size graduations keyed to relative position of said elements for movably adjusting positions of said elements while visually assessing fit of prosthesis size.

7. An alignment jig according to claim 1, wherein the body moves side to side to adjust position of a prosthesis in relation to offset of the epicondyles.

8. An alignment jig for locating a cutting block or the like to prepare a bone ending for receiving a prosthetic joint component, wherein the bone ending possesses medial and lateral epicondyles, the jig comprising a body configured to lie adjacent a distal prepared femoral bone surface at least first and second epicondylar engagers mechanically extending from the body, the engagers being configured to selectively contact and engage opposed epicondylar regions of the bone and hold the body aligned along the epicondylar axis at said surface an A/P positioning assembly movably extending from the body and being positionable in contact with the bone to set an A/P position of the body, and a tool guide carried by the body said body being lockingly movable with respect to the epicondylar engagers and the A/P positioning assembly to orient and position the body so as to align the tool guide for forming locator holes in the bone aligned relative to the epicondylar axis.

9. A method for locating a sawcut template or the like to prepare a bone ending for receiving a prosthetic joint component during installation of a prosthesis, wherein the bone ending possesses medial and lateral epicondyles defining an epicondylar axis, and posesses at least some epicondylar connective tissue, the method comprising the steps of providing a body configured to lie adjacent a distal prepared femoral bone surface and having a structure for positioning a tool to cut a bone alignment feature at said surface to determine placement of the component on the bone ending, and providing an alignment assembly moveably coupled to the body and alignable with respect to medial and lateral such that when so aligned the alignment assembly holds the body in alignment relative to the epicondylar axis, so that the tool is positioned to cut said bone alignment feature in alignment relative to the epicondylar axis, thereby enhancing soft tissue balance of the installed prosthesis.

10. The method of claim 9, further comprising the step of movably extending an A/P positioning assembly from the body into contact with the bone to set A/P displacement of the feature.

11. The method of claim 10, further comprising the step of lockingly moving the body with respect to the alignment assembly and the A/P positioning assembly to adjust and lock the location of the body across the surface while maintaining the bone feature cut aligned relative to the epicondylar axis.

12. The method of claim 9, wherein the body includes a drill guide configured to place drill holes for receiving locator pins of a cutting block.

* * * * *